(12) United States Patent
Hasegawa (10) Patent No.: US 10,687,989 B2
(45) Date of Patent: Jun. 23, 2020

(54) DISPOSABLE WEARING ARTICLE

(71) Applicant: Unicharm Corporation, Shikokuchuo-shi, Ehime (JP)

(72) Inventor: Mari Hasegawa, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 358 days.

(21) Appl. No.: 15/740,862

(22) PCT Filed: May 19, 2016

(86) PCT No.: PCT/JP2016/064841
§ 371 (c)(1),
(2) Date: Dec. 29, 2017

(87) PCT Pub. No.: WO2017/002478
PCT Pub. Date: Jan. 5, 2017

(65) Prior Publication Data
US 2018/0193207 A1    Jul. 12, 2018

(30) Foreign Application Priority Data

Jun. 30, 2015   (JP) ................. 2015-132234

(51) Int. Cl.
*A61F 13/15*      (2006.01)
*A61F 13/49*      (2006.01)
(Continued)

(52) U.S. Cl.
CPC ...... *A61F 13/49012* (2013.01); *A61F 13/494* (2013.01); *A61F 13/496* (2013.01);
(Continued)

(58) Field of Classification Search
CPC .............. A61F 13/49012; A61F 13/494; A61F 13/496; A61F 13/4902; A61F 2013/49033; A61F 2013/49041
(Continued)

(56) References Cited

U.S. PATENT DOCUMENTS 5,593,401 A * 1/1997 Sosalla ............. A61F 13/49011
                                                     604/385.28
6,258,076 B1 * 7/2001 Glaug ............... A61F 13/49466
                                                     604/385.01
(Continued)

FOREIGN PATENT DOCUMENTS

JP     2002-282303 A    10/2002
JP      2003-79659 A     3/2003
(Continued)

OTHER PUBLICATIONS

International Search Report in PCT/JP2016/064841, dated Aug. 2, 2016. 4pp.

*Primary Examiner* — Jacqueline F Stephens
(74) *Attorney, Agent, or Firm* — Hauptman Ham, LLP (57) ABSTRACT

Disclosed is a disposable wearing article which can effectively prevent lateral leakage of body exudates by planarly fitting an outer flap positioned laterally outside of an absorbent core included in an absorbent panel on the body of a wearer with the outer flap pulled laterally outside of the article. In the article, the absorbent panel includes the absorbent core extending to front and rear waist regions centering on a crotch region and a pair of outer flaps extending laterally outside of the absorbent core. At least the front waist region of the front and rear waist regions includes a waist elastic area which is elastically contractible in the lateral direction and a pair of elastic strips which is elasti-
(Continued)

cally contractible, and the elastic strips each have an outer fixing end fixed on the body facing surface of the chassis.

12 Claims, 11 Drawing Sheets

(51) Int. Cl.
*A61F 13/494* (2006.01)
*A61F 13/496* (2006.01)

(52) U.S. Cl.
CPC . *A61F 13/4902* (2013.01); *A61F 2013/49033* (2013.01); *A61F 2013/49041* (2013.01)

(58) Field of Classification Search
USPC ............ 604/385.24, 385.25, 385.26, 385.27, 604/385.28, 385.29, 385.3, 385.31
See application file for complete search history.

(56) References Cited

U.S. PATENT DOCUMENTS

| | | | |
|---|---|---|---|
| 6,447,495 B1* | 9/2002 | Luizzi ................... | A61F 13/476 604/385.03 |
| 2002/0115979 A1* | 8/2002 | Ikeda ................ | A61F 13/15203 604/385.101 |

FOREIGN PATENT DOCUMENTS

| | | |
|---|---|---|
| JP | 2003-126142 A | 5/2003 |
| JP | 2010-187777 A | 9/2010 |
| WO | 2013/108792 A1 | 7/2013 |

* cited by examiner

DISPOSABLE WEARING ARTICLE

RELATED APPLICATIONS

The present application is a National Phase of International Application Number PCT/JP2016/064841, filed May 19, 2016, which claims priority to Japanese Application Number 2015-132234, filed Jun. 30, 2015.

TECHNICAL FIELD

The present disclosure relates to disposable wearing articles such as disposable diapers, disposable diaper covers and the like.

BACKGROUND ART

Conventionally, Patent Literature 1 discloses a disposable wearing article having an elastic chassis forming the outer shape, an absorbent panel disposed on the body facing surface of the chassis and including an absorbent core, and a pair of barrier cuffs extending along the lateral outside edges of the absorbent core.

CITATION LIST

[Patent Literature] JP 2003-79659 A

SUMMARY OF INVENTION

Technical Problem

In the wearing article disclosed in PTL 1, a pair of elastic strips each having an inner end joined to a distal edge of each of the barrier cuffs and an outer end thereof joined on the body facing surface of the chassis are disposed in the front and rear waist regions, and a pair of barriers for preventing body exudates from leaking sideways is formed by the pair of barrier cuffs capable of spacing away from the body facing surface of the absorbent panel toward the body of a wearer.

However, the elasticity of the chassis may degrade the absorption performance of the absorbent panel due to longitudinal creases formed by contraction of the ends of the absorbent core in the lateral direction under a contractible force of the chassis. Further, the side flaps of the article extending laterally outward from the lateral edges of the absorbent core of the absorbent panel are lower than the position area of the absorbent core in stiffness, and is easy to laterally contract under a contractible force of the chassis. This causes body exudates from leaking sideways due to the gaps formed between the body of a wearer and the article when worn in such a contracted state, i.e., a creased state of the side flaps.

The present invention is directed to an improvement of conventional disposable wearing articles in which barrier flaps disposed laterally outside of an absorbent core are pulled outward so that the barrier flaps may come in planar contact with the body of a wearer, thereby making it possible to effectively prevent body exudates from leaking sideways.

Solution to Problem

In order to solve the above problems, the present invention is featured in a disposable wearing article which has a longitudinal direction and a lateral direction, and comprises a chassis including a body facing surface, a non-body surface, a first waist region which is one of front and rear waist regions, a second waist region which is another of the front and rear waist regions, a crotch region extending between the front and rear waist regions, an absorbent panel disposed on the body facing surface of the chassis, and side seams respectively coupling both lateral edges of the first waist region and both lateral edges of the second waist region.

In the disposable wearing article according to the present invention, the absorbent panel includes an absorbent core extending to the front and rear waist regions centering on the crotch region and a pair of outer flaps each extending longitudinally along a side edge of the absorbent core, at least the first waist region of the first and second waist regions includes a waist elastic area which is elastically contractible in the lateral direction, a pair of elastic strips which are elastically contractible in the lateral direction, and the elastic strips have an inner fixing end fixed to the outer flap of the absorbent panel and an outer fixing end fixed to the body facing surface of the chassis.

The outer flap of the absorbent panel is fixed to the body facing surface of the chassis, and the inner fixing end of the elastic strip of the absorbent panel is fixed to the body facing surface of the outer flap. With this embodiment, the outer flap fixed to the absorbent panel is contracted in the lateral direction under contractible action of the waist region, and can come in planar contact with the body of a wearer by being pulled outward under contraction of the elastic strip.

At least a part of the outer flap of the absorbent panel is unfixed to the body facing surface of the chassis, and the inner fixing end of the elastic strip is fixed to the non-body facing of the outer flap. With this embodiment, when part of the outer flap is unfixed to the chassis, the absorbent panel and the outer flap may positionally be displaced, but they can properly be positioned by the elastic strip.

A tensile stress in the lateral direction of the elastic strip is higher than a tensile stress in the lateral direction of the waist elastic area. With this embodiment, the elastic strip does not extend to its full length, and the waist region can extend in the required length to conform to the waist of a wearer without stopping stretching.

The outer flap of the absorbent panel includes a side elastic area which is elastically contractible in the longitudinal direction, and the inner fixing end of the elastic strip is overlapped with the side elastic area in planar view. With this embodiment, the outer flap improves fittability to the body of a wearer.

The outer fixing end of the elastic strip is positioned inside in the lateral direction of the side seam, and a dimension in the lateral direction of the elastic strip is more than 50% of a space dimension in the lateral direction of from the inner fixing end to the side seam. With this embodiment, the elastic strip having a relatively large elastic area can reliably pull the outer flap outward in the lateral direction in the worn state of the article.

The outer fixing end of the elastic strip extends to the side seam. With this embodiment, the elastic strip is difficult to be removed from the chassis during wearing of the article due to the elastic strip being fixed together with other components of the waist region at the side seam.

The absorbent panel includes a pair of barrier cuffs, and the barrier cuffs are each positioned more inside in the lateral direction than the inner fixing end of the elastic strip. With this embodiment, the barrier cuffs of the absorbent panel can effectively prevent lateral leakage of body exudates.

The elastic strip extends more outside in the longitudinal direction than a longitudinal end of the absorbent core. With this embodiment, the elastic strip can suppress a vicinity of a longitudinal end of the absorbent core which is a change part of stiffness in the waist region, and can reduce formation of a level difference at the change part.

The pair of elastic strips is disposed on the second waist region, and the pair of elastic strips positioned on the first waist region and the pair of elastic strips positioned on the second waist region are respectively joined to each other at the side seams. With this embodiment, the elastic strips disposed to the first and second waist regions on both sides of the article are contiguous to each other around the first and second waist regions, and the outer flaps can be pulled out in a well-balanced state.

The pair of elastic strips are disposed on the second waist region, and a dimension in the longitudinal direction of each of the elastic strips positioned on the first waist region is equal to or larger than a dimension in the longitudinal direction of each of the elastic strips positioned on the second waist region. With this embodiment, even when the front and rear ends of the absorbent core are differently positioned in the longitudinal direction, the front and rear ends can be covered with each of the elastic strips by adjusting suitably the dimension in the longitudinal direction of the elastic strips.

The elastic strip is temporally fixed on the body facing surface of the chassis. With this embodiment, the elastic strip will not be removed from the chassis during carrying around of the diaper, and may also not be caught by the wearer's toes when putting on.

Advantageous Effects

With one or more of the embodiments according to the disposable wearing article of the present invention, the outer flaps of the absorbent panel are pulled outward in the lateral direction in a planar form under contraction act of the elastic strips, and thus lateral leakage of body exudates is effectively prevented by putting in planar contact with the wearer's body of the elastic strips.

BRIEF DESCRIPTION OF DRAWINGS

The drawings illustrate specific embodiments of the present invention including optional and preferred embodiments as well as essential features of the invention, in which

FIG. 6A illustrates a body facing surface of a front waist region of the disposable diaper before put on, FIG. 6B illustrates the body facing surface of the front waist region when put on;

FIG. 7 illustrates a cross-section view similar to FIG. 3 before put on;

DESCRIPTION OF EMBODIMENTS

The embodiments described below relate to a diaper as an example of a disposable wearing article as illustrated in FIGS. 1 through 11, including both optional and preferred features as well as those features which are essential features of the present invention.

Figure 1:
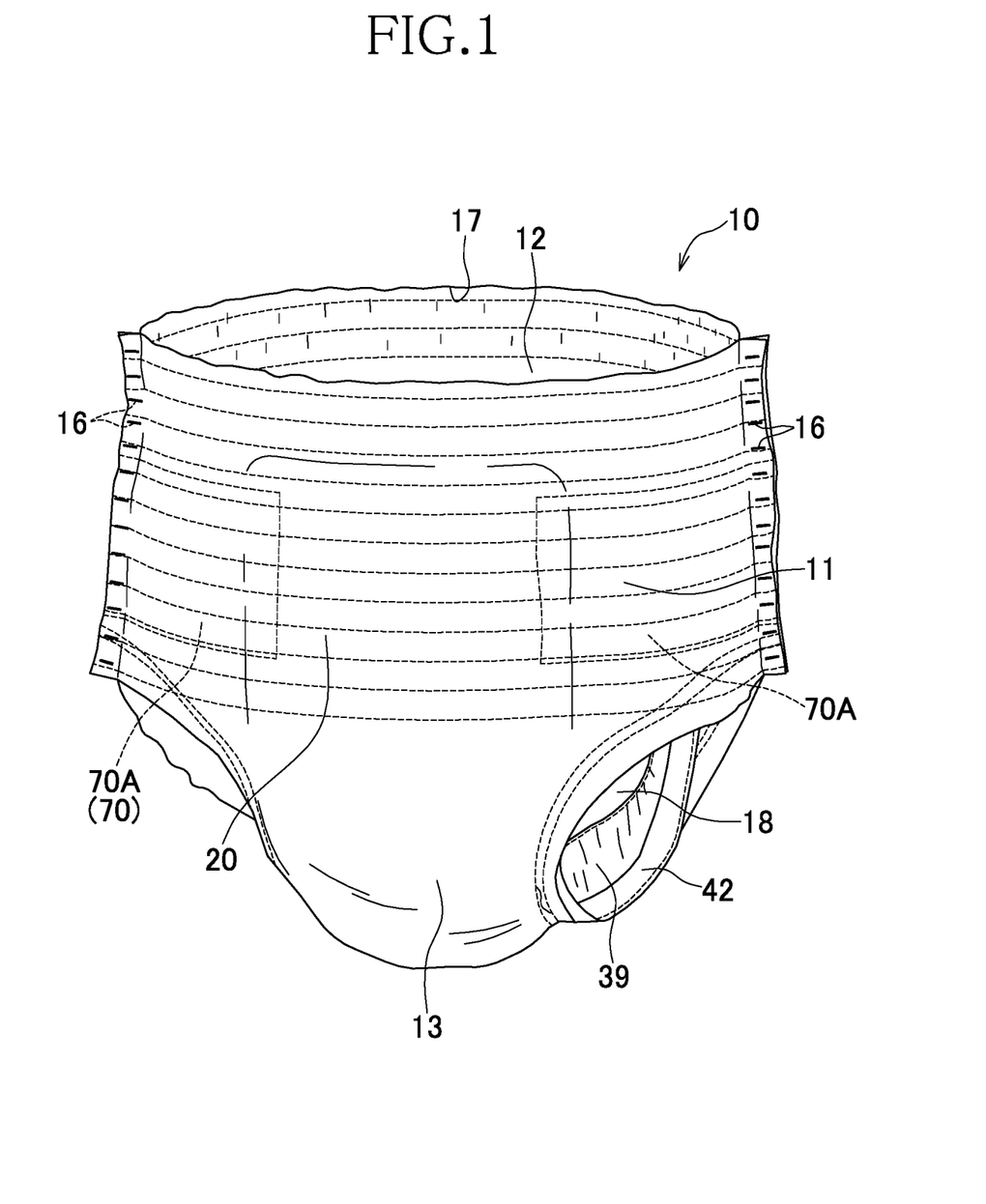
FIG. 1 illustrates a perspective view from the front of a disposable diaper as an example of a disposable wearing article according to the first embodiment of the present invention.
Figure 2:
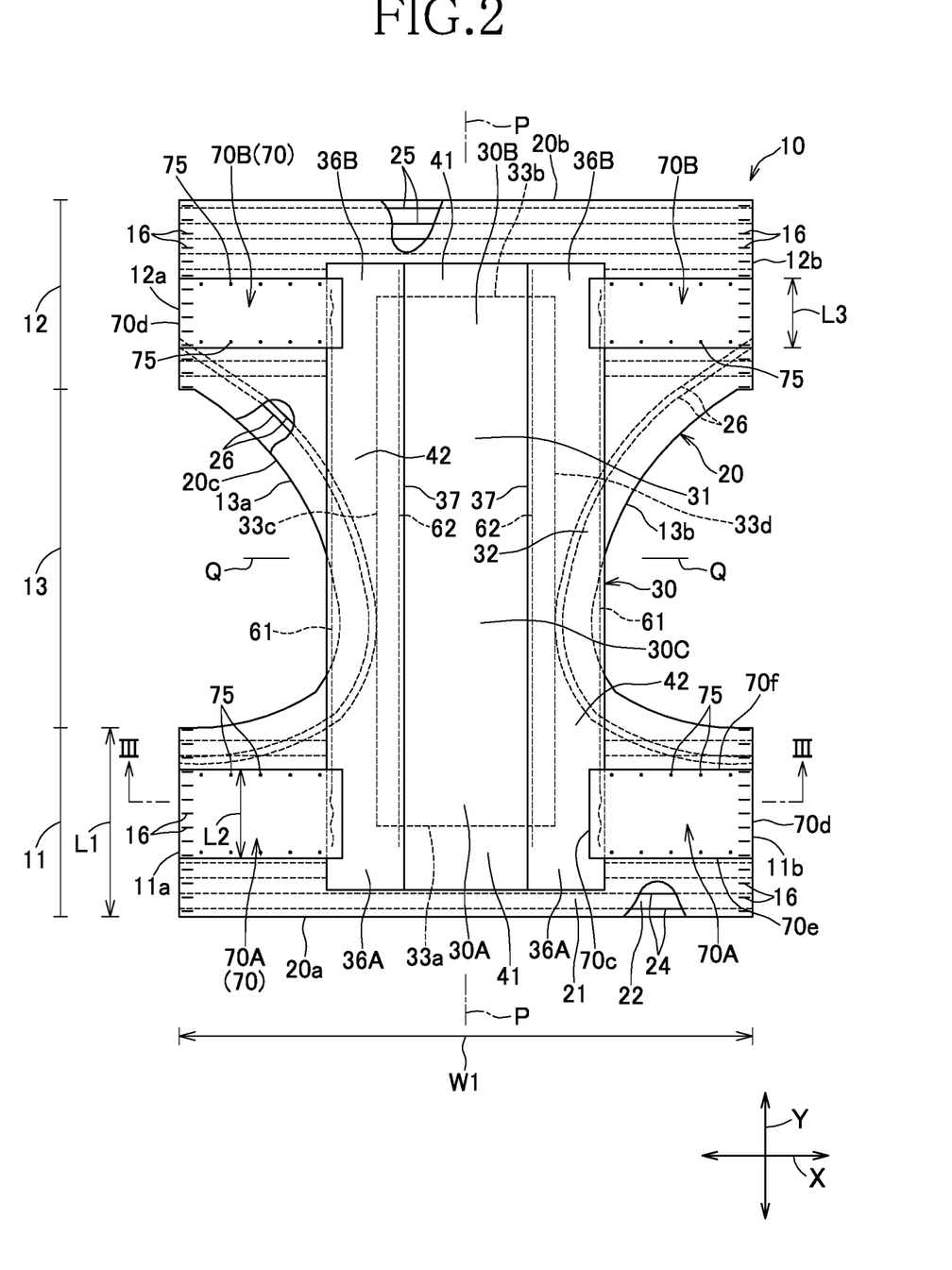
FIG. 2 illustrates a partially cutaway opened plan view from the inside of the diaper in which respective elastic members are stretched at the maximum in the longitudinal and lateral directions, i.e., to the extent that gathers formed in the diaper under contraction of the respective elastic members disappears.
Figure 3:
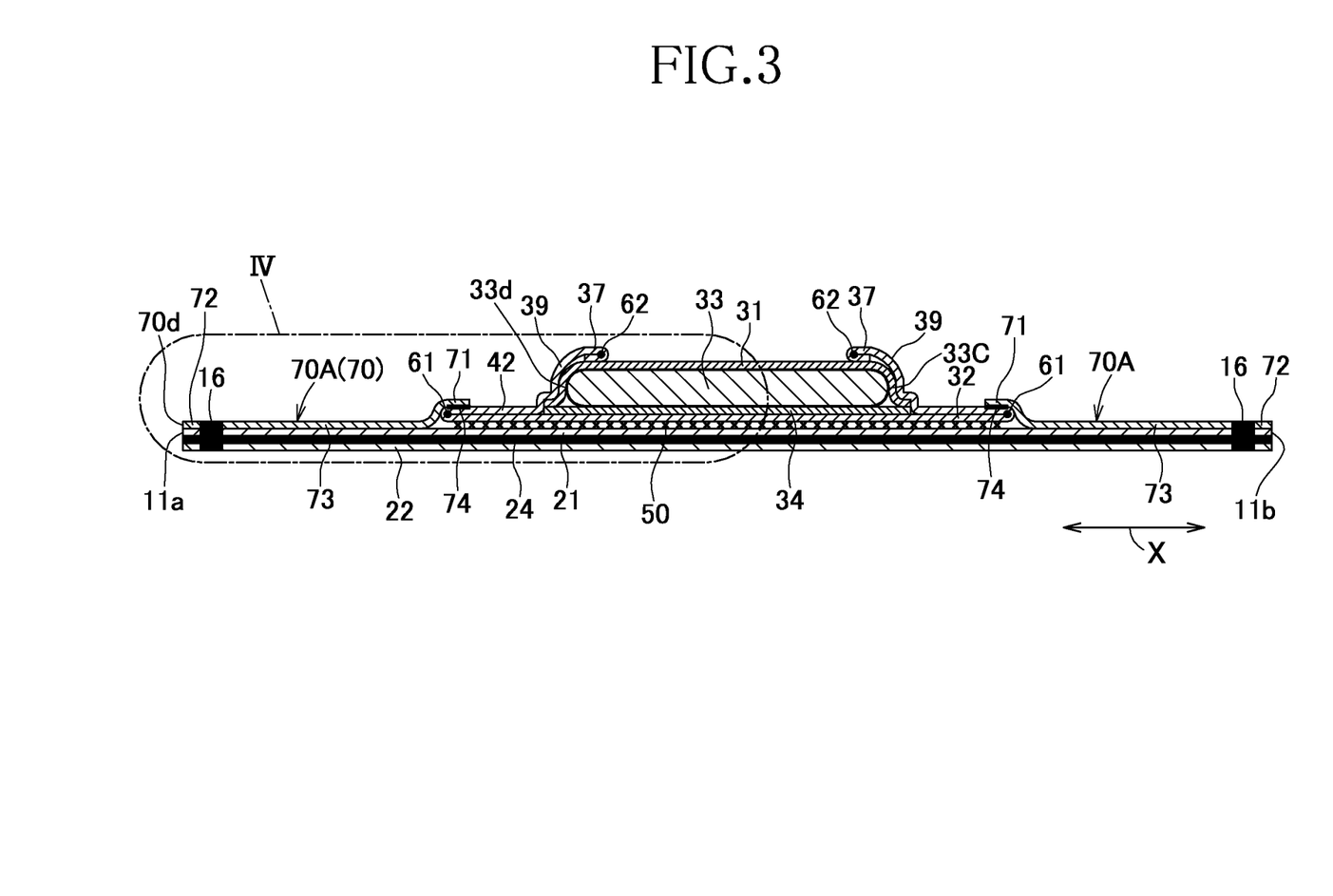
FIG. 3 illustrates a cross-sectional view along line of FIG. 2.

With reference to FIGS. 1 through 3, a disposable diaper 10 as an example of a disposable wearing article has a longitudinal direction Y, a lateral direction X, a longitudinal center line P-P along the longitudinal direction Y and a lateral center line Q-Q along the lateral direction X, and may include a body facing surface, a non-body surface opposed to the body facing surface, a front waist region 11, a rear waist region 12, a crotch region 13 extending between the front and rear waist regions 11 and 12, a chassis (base panel) 20 forming an outer shape of the diaper 10 and an absorbent panel 30 disposed on the body facing surface of the chassis 20. The longitudinal center line P-P bisects a dimension in the lateral direction X of the diaper 10, the lateral center line Q-Q bisects a dimension in the longitudinal direction Y of the diaper 10, and the diaper 10 is symmetrical about the longitudinal center line P-P.

The chassis 20 is stretchable/contractible at least in the lateral direction X, and may have front and rear ends 20a and 20b opposed to each other in the longitudinal direction Y and both lateral edges extending in the longitudinal direction Y between the front and rear ends 20a and 20b. Both lateral edges 13a and 13b of the chassis 20 (both lateral edges of the diaper 10) may be concave in the crotch region so as to fit about the thighs of a wearer. Both lateral edges may include lateral edges 11a and 11b, and 12a and 12b linearly extending in the longitudinal direction Y in the front and rear waist regions 11 and 12, and lateral edges 13a and 13b curvedly extending between the lateral edges 11a and 12a, and 11b and 12b. Both lateral edges of the front waist region 11 and both lateral edges of the rear waist region 12 may respectively be coupled with each other at side seams 16 made at intervals in the longitudinal direction Y to define a waist opening 17 and a pair of leg openings 18. The side seams 16 may be made by well-known heat welding means including het sealing and supersonic sealing techniques.

The chassis 20 may include a liquid impermeable inner layer 21 positioned on the side of the body facing surface, a liquid impermeable outer layer 22 positioned on the side of the non-body facing surface. The chassis 20 may have front and rear waist elastic members 24 and 25 and leg elastic members 26 each composed of a plurality of tread-like, strand-like or string-like elastic materials and disposed in a contractible manner under tension between the inner and outer layers 21 and 22. The front and rear waist elastic members 24 and 25 may respectively extend in the lateral direction X between both lateral edges 11a and 11b, and 12a and 12b. The leg elastic members 26 may curvedly extend along the lateral edges 13a and 13b between the lateral edges 11a and 12a, and 11b and 12b of the front and rear waist regions 11 and 12, respectively. Referring to FIG. 2, a dimension W1 in the lateral direction X of the diaper 10 may be about 350 mm to about 450 mm, and a dimension L1 in the longitudinal direction Y of the front waist region 11 (the same as that of the rear waist region 12) is about 70 mm to about 140 mm.

The front and rear waist regions 11 and 12 may respectively have front and rear waist elastic areas which are contractible in the lateral direction X under contraction of the front and rear waist elastic members 24 and 25. Similarly, the crotch region 13 may have leg waist elastic areas which are contractible along the lateral edges 13a and 13b under contraction of the leg elastic members 26.

The inner and outer layers 21 and 22 may be constructed of well-known fibrous nonwoven fabrics such as SMS (spunbonded-meltbrown-spunbonded) fibrous nonwoven fabrics, spunbonded fibrous nonwoven fabrics and air through fibrous nonwoven fabrics, or well-known plastic sheets, or well-known laminated sheets made of fibrous nonwoven fabrics, or well-known laminated sheets made of fibrous nonwoven fabrics and plastic sheets. The inner and outer layers 21 and 22 may be joined to each other with hot melt adhesive applied to the inner surface of at least one of them or by heat welding them together. The front and rear waist elastic members 24 and 25 and the leg elastic members 26 may respectively have a fineness of about 300 dtex to about 500 dtex, a space interval (pitch) between each of them in the longitudinal direction Y of about 2.0 mm to about 5.0 mm, and may contractibly be secured between the inner and outer layers 21 and 22 in a condition stretched at about 2.2 times to 2.6 times the natural length of them.

Figure 4:
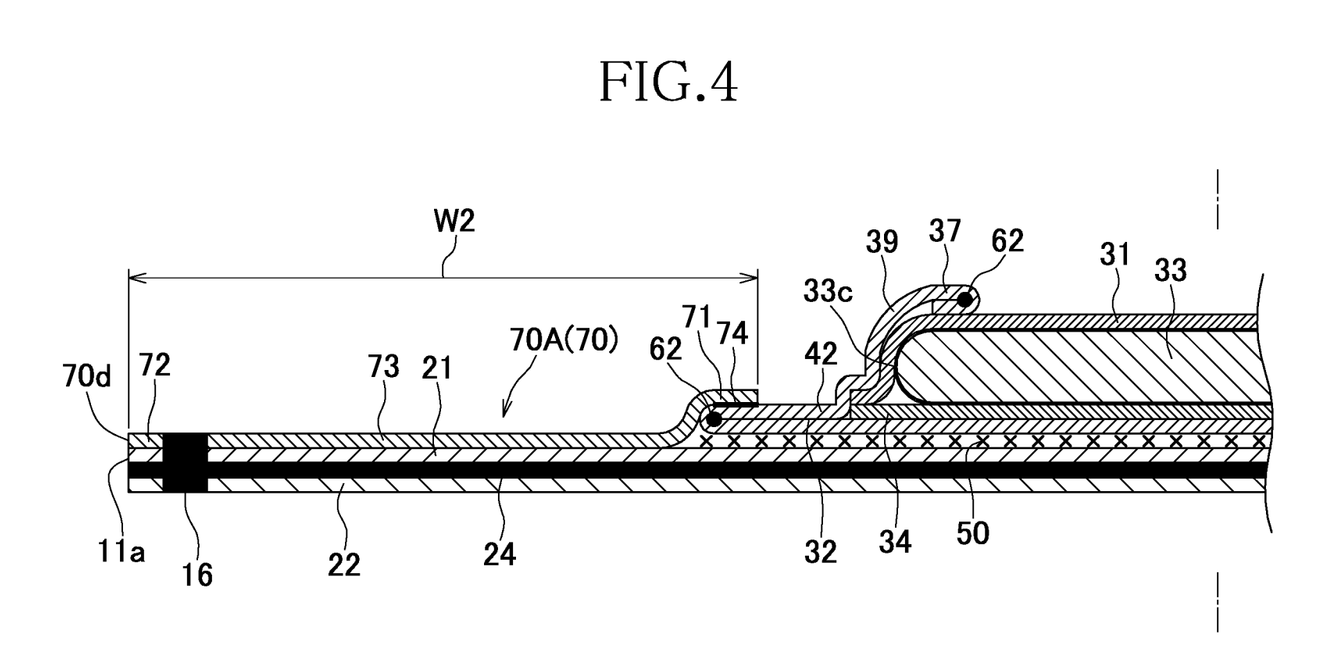
FIG. 4 illustrates an enlarged view of an area encircled by line 1V of FIG. 3.

With reference to FIGS. 3 and 4, the absorbent panel 30 may be shaped into a longitudinally long rectangular, and may include a liquid permeable bodyside liner 31, a liquid impermeable covering layer 32, an absorbent core 33 interposed between the bodyside liner 31 and the covering layer 32 and a leakage barrier layer 34 disposed between the absorbent core 33 and the covering layer 32.

The absorbent core 33 may have front and rear end edges 33a and 33b and both side edges 33c and 33d linearly extending in the longitudinal direction Y between the front and rear end edges 33a and 33b, and may extend to the front and rear waist regions 11 and 12 centering on the crotch region 13. The absorbent core 33 may include semi-rigid core materials formed from a mixture of wood fluff pulp and superabsorbent polymer particles and a liquid diffusive wrapping sheet such as tissue paper for covering the absorbent core 33. The wrapping sheet also may have shape retaining function for the absorbent core 33. The leakage barrier layer 34 may be formed of liquid impermeable but breathable plastic films or fibrous nonwoven fabrics and has preferably a size capable of covering the entire bottom of the absorbent core 33. Optionally, a liquid permeable fibrous layer having cushioning and liquid diffusive properties may be disposed between the bodyside liner 31 and the absorbent core 33.

The absorbent panel 30 may have a front end 30A lying on the front waist region 11, a rear end 30B lying on the rear waist region 12 and a middle 30C of the crotch region 13 between the front and rear ends 30A and 39B. The absorbent panel 30 may further have end flaps 41 extending outside in the longitudinal direction Y of the front and rear ends 33a and 33b of the absorbent core 33 and outer flaps (side flaps) 42 extending outside in the lateral direction X of the absorbent core 33, and absorbent panel 30 may be fixed on the chassis 20 through a joining area 50 defined by hot melt adhesive applied to the entire surface of the chassis 20 facing the absorbent panel 30.

The covering layer 32 may have both lateral areas extending outside in the lateral direction X. By both lateral areas, formed are inner flaps 39 and the outer flaps 42 by being folded on the sides of the longitudinal center line P-P (laterally inward), respectively. The inner flaps 39 may each have a front end 39A and a rear end 36B as part of each of the end flaps 41 and fixed on the bodyside liner 31 in the front and rear waist regions 11 and 12, and folded distal edges 37.

The outer flaps 42 may each be arranged with thread-like, string-like or strand-like outer flap elastic members 61 extending in the longitudinal direction Y in a contractible manner under tension. Similarly, the distal edges 37 of the inner flaps 42 may each be arranged with thread-like, string-like or strand-like inner flap elastic members 62 extending in the longitudinal direction Y in a contractible manner under tension. The outer flaps 39 each having the distal edge 37 may be spaced away from the body facing surface of the bodyside liner 31 toward the groins of a wearer under a contractible force of the inner flap elastic members 62 to give a barrier function to the inner flaps 39 when the diaper is worn, thereby preventing body exudates from leaking sideways. The outer flaps 42 may planarly come in contact with the thighs of a wearer under a contractible force of the outer flap elastic members 61 in a state extended outward in the lateral direction X at the leg openings to prevent body exudates from leaking sideways. In this way, the absorbent panel 30 can effectively prevent body exudates from leaking sideways by cooperative function of the inner flaps 39 contacted with the groins spacing away from the bodyside liner and the outer flaps 42 contacted with the thighs. It should be noted here that the inner flaps 39 and the outer flaps 42 may be formed of liquid permeable or liquid impermeable sheets separate of the covering layer 32.

With reference to FIG. 2 through 4, the front and rear waist regions 11 and 12 may respectively be disposed with elastic strips 70 laterally extending from lateral edges 11a and 11b, and 12a and 12b toward the longitudinal center line P-P. The elastic strips 70 may include a pair of elastic strips 70A disposed in the front waist region 11 and a pair of elastic strips 70B disposed in the rear waist region 12. The elastic strips 70 may be symmetrical about the longitudinal enter line P-P and have a laterally long rectangle defined by inner and outer end edges 70c and 70d extending straight in the longitudinal direction, and both lateral side edges 70e and 70f extending straight in the lateral direction X. The elastic strips 70 may each have an inner fixed end 71 fixed to the outer flap 42, an outer fixed end 72 fixed to the body facing surface of the chassis 20, and an elastic area 73 positioned between the inner and outer fixed ends 71 and 72. The inner fixed end 71 of the elastic strip 70 may be fixed by a joining part 74 coated with hot melt adhesive and the outer fixed end 72 of the elastic strip 70 may be fixed together with the inner and outer layers 21 and 22 at the lateral edge of the front and rear waist regions 11 and 12 through the side seam 16.

The elastic strips 70 may be formed of elastic fibrous nonwoven fabrics which are stretchable and contractible at least in the lateral direction X. The elastic fibrous nonwoven fabrics may include, for example, stretchable and contractible fibrous nonwoven fabrics such as spun-bonded fibrous nonwoven fabrics, air-through fibrous nonwoven fabrics and needle-punched fibrous nonwoven fabrics constructed of elastic fibers (elastic filaments) which are made by well-known various manufacturing methods. Materials of the elastic fibers may include thermoplastic elastomer and rubber, particularly, when the thermoplastic elastomer is used as the materials, it is possible to melt-spinning by using an extruder as with conventional thermoplastic resins. The fibers obtained in such way are suitable to be used to the elastic fibrous nonwoven fabrics because the elastic strips 70 made of such nonwoven fabrics are easy to heat-weld together with the inner and outer layers 21 and 22 at the side seams 16.

The elastic strips 70 may be formed of an elastic composite fibrous nonwoven fabric constructed of two inelastic fibrous nonwoven fabrics and a plurality of elastic threads, as long as the elastic strips 70 are stretchable and contractible in the lateral direction X. In this regard, when the elastic strips 70 are formed of the elastic nonwoven fabric, the elastic strips 70 may come in direct contact with the skin of a wearer and provide good texture and keep the skin in a dry state by transferring the sweat on the skin to the elastic strips 70 because minute irregularities formed on the surface of the elastic strips 70 under contraction thereof come in close contact with the skin. In particular, the areas in which the elastic strips 70 are disposed on the inner surface of the overlapped inner and outer layers 21 and 22 are easy to get stuffy, and thus it is preferable to quickly transfer the sweat on the skin to the elastic fibrous nonwoven fabric. The elastic strips 70 formed of the elastic fibrous nonwoven fabric may provide such a preferred state. However, even when the elastic strips 70 are formed of the elastic composite fibrous nonwoven fabric including the elastic threads as described above, the elastic composite fibrous nonwoven fabric may achieve the transferring effect of the sweat on the skin in substantially the same as the elastic fibrous nonwoven fabric, at least by setting the arrangement pitch of the elastic threads in the elastic composite fibrous nonwoven fabric to be less than 3.0 mm so that minute irregularities may be formed on the elastic composite fibrous nonwoven fabric under contraction.

With reference to FIG. 2, the elastic strips 70 may each have the elastic area 73 temporally fixed to the body facing surface of the chassis 20 by more than one discrete spaced temporal fixing sites 75 arranged in the lateral direction X. The temporal fixing sites 75 may be provided by application of a small amount of hot-melt adhesive or heat debossing processing so that the elastic strips 70 may detachably be affixed on the inner layer 21 defining the body facing surface of the chassis 20. In this way, since the elastic strip 70 is temporally fixed, it is possible to prevent the transfer of the chassis 20 from being hindered due to the elastic areas 73 of the elastic strip 70 separating from the chassis 20 in the manufacturing process of the diaper 10 or the toes of a wearer from being caught by the elastic area 73 separated from the chassis 20. Further, since the temporal fixing sites 75 are arranged in more than one discrete spaced state in the lateral direction X, the fixing of the temporal fixing sites 75 may easily be released by peeling up the elastic strip 70 from the chassis 20 when the diaper 10 is put on a wearer, compared to the instance where the temporal fixing sites 75 continuously extending in the lateral direction X.

Figure 5:
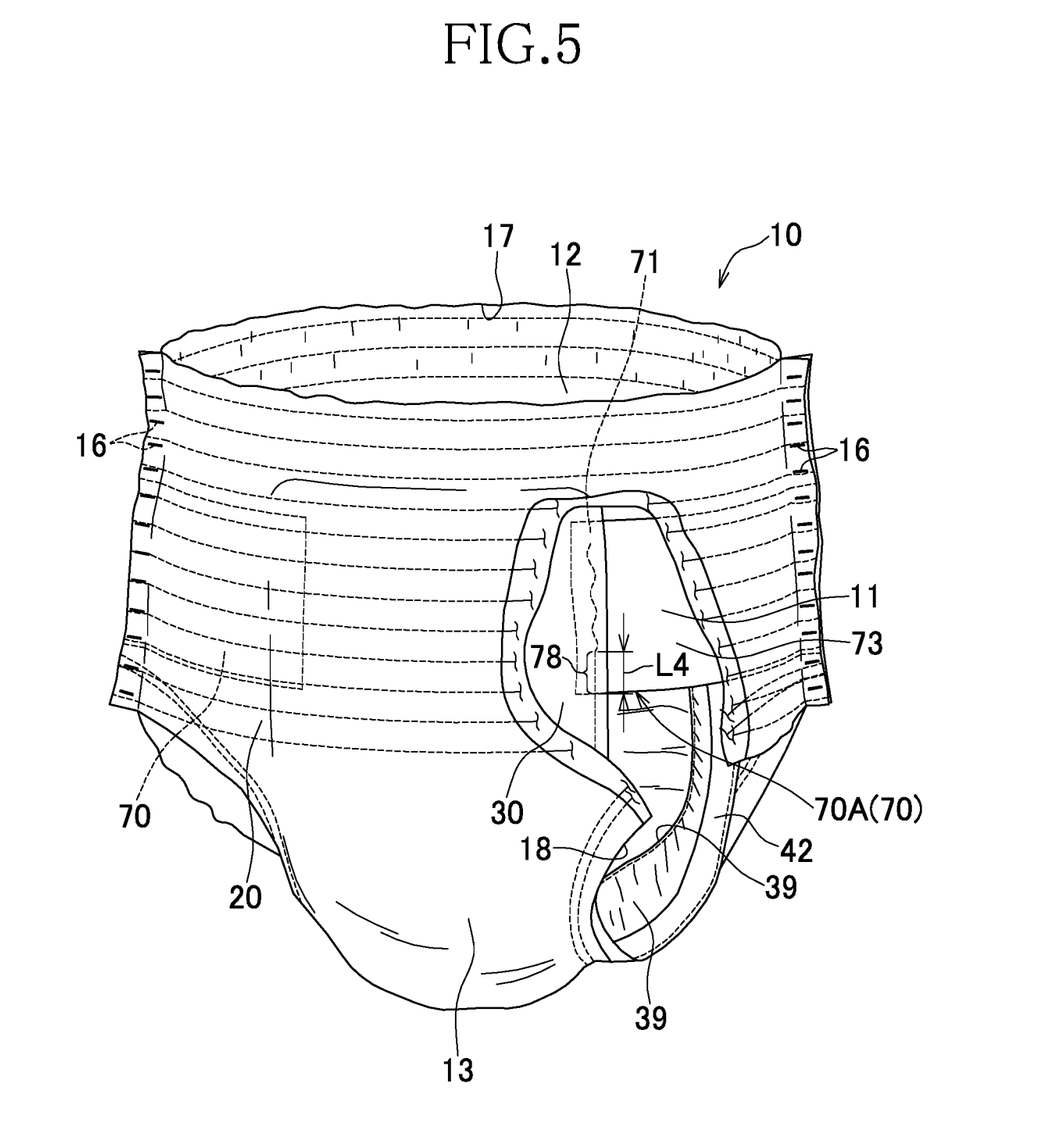
FIG. 5 illustrates a partially enlarged perspective view from the front of the disposable diaper.
Figure 6A:
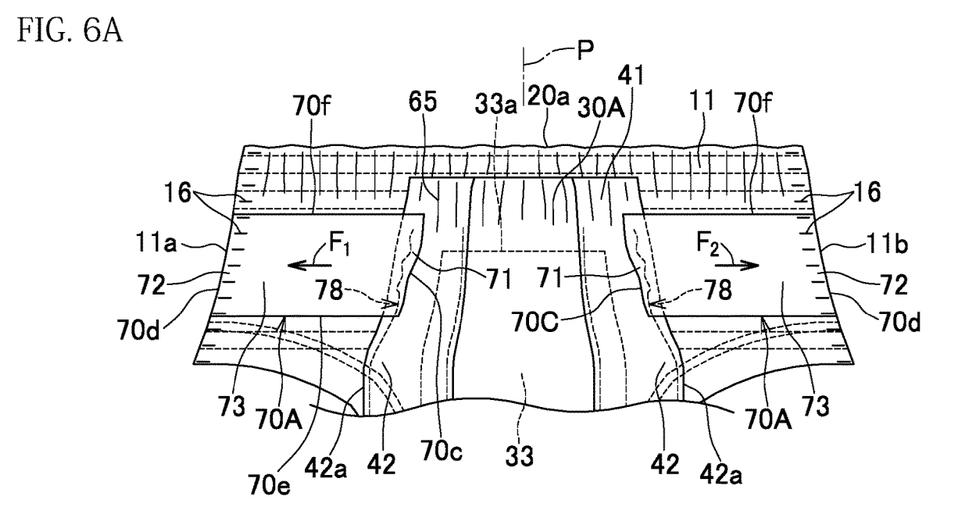
Figure 6B:
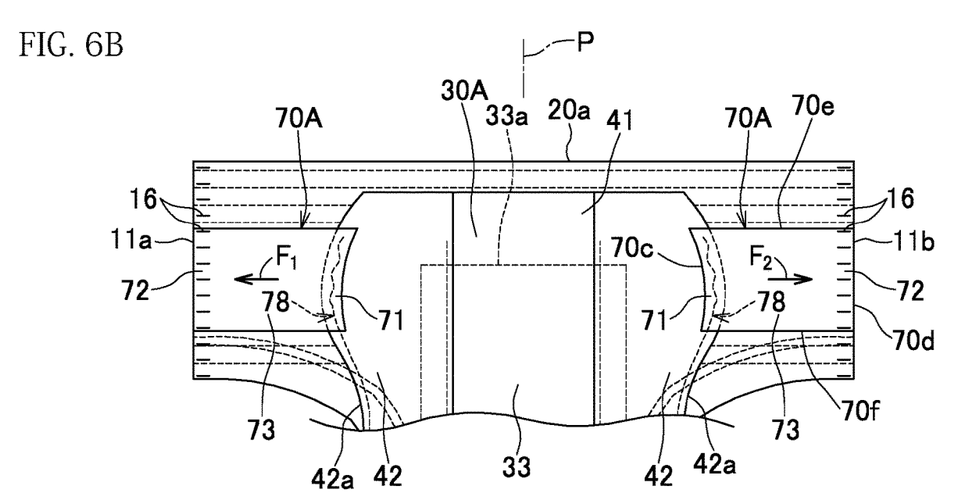
Figure 7:
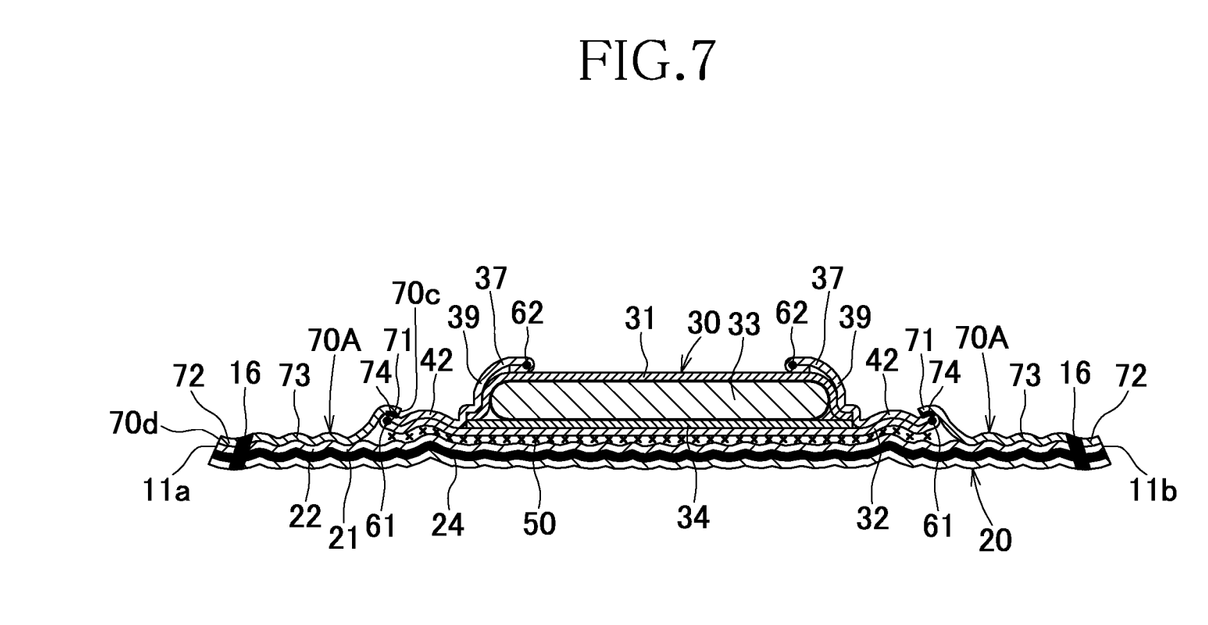

FIG. 5 illustrates a partially enlarged perspective view from the front of the disposable diaper; FIG. 6A illustrates a body facing surface of a front waist region of the disposable diaper before put on, FIG. 6B illustrates the body facing surface of the front waist region when put on; and FIG. 7 illustrates a cross-section view similar to FIG. 3 before put on. The description below relates to the elastic strips 70A disposed on the front waist region 11. The elastic strips 70B disposed on the rear waist region 12 may have the same configuration and technical effects as those in the former, and the description of the latter is omitted below.

With reference to FIG. 6A, a front end 30A of the absorbent panel 30 is gathered in the lateral direction under contraction action of the front waist elastic area in a state where multiple gathers extending in the longitudinal direction Y are formed. Similarly, the outer flaps 42 of the absorbent panel 30 are gathered in the lateral direction X while the outside edges 42a of the outer flaps 42 are tilted toward the longitudinal center line P-P.

When the front end 30A of the absorbent panel 30 are deformed in such gathered state, the absorbent core 33 is also formed with gathers which may degrade the absorption performance, as well as the outer edges 42a of the outer flaps 42 may be twisted or curled due to the gathering of the outer flaps 42 in the lateral direction X. If the diaper 10 is put on the body of a wearer in such deformed state of the outer flaps 42, the outer flaps 42 may not planarly come in contact with the thighs of the wearer about the leg openings 18, and gaps may be formed between the outer flaps 42 and the thighs, which may cause the leakage of body exudates.

FIG. 5 and FIG. 6B, when the diaper 10 is worn, the outer flaps 42 are pulled outward in the lateral direction X by stretching of a pair of the elastic strips 70, and the outer side edges 42a of the outer flaps 42 positioned adjacent to the inner fixed ends 71 may be spread out in a convexly curved shape so as to space away from the longitudinal direction X toward the outside in the lateral direction X, and parts of the outer flaps 42 extending from the spread parts toward the crotch region 13 may planarly come in contact with the thighs of a wearer. Further, by stretching of the paired elastic strips 70, the absorbent panel 30 may be pulled out under tensile forces F1 and F2 exerted in the opposite lateral directions to each other, so that the paired outer flaps 42 are laterally pulled out, the end flap 41 and the front end of the absorbent core 33 positioned between the paired outer flaps 42 are laterally spread, the gathers formed on the end flap 41 and the front end become smaller, and the absorption performance of the absorbent core 33 should not be degraded.

In the present preferred embodiment, the outer flaps 42 are fixed on the body facing surface of the chassis 20, which may be gathered in the lateral direction X under contraction of the front waist elastic are. However, the inner fixed ends 71 of the elastic strips 70A are fixed to the body facing surface of the outer flaps 42 and the outer fixed ends 72 are fixed on the body facing surface of the chassis 20 in such fixed condition, the elastic areas 73 positioned between both fixed ends 71 and 72 are stretched in the lateral direction X. Thus, the outer flaps 42 can be pulled out in the lateral direction X so that the gathers can be reduced.

With reference to FIGS. 2 and 3, the outer flaps 42 may each have a side elastic area disposed with an elastic member 61 (except for elastic part of the elastic member 61), and the side elastic area may be overlapped with the inner fixed end 71 of the elastic strip 70 in planar view. When the diaper 10 is worn, the outer flap 42 may be pulled out in the lateral direction X by the elastic strip 70 while being stretched in the longitudinal direction Y by the side elastic area. Thus, the gathers formed on the outer flap 42 can be expanded so that the outer strip 42 can come in contact with the wearer's thigh. Further, the inner fixed ends 71 of the elastic strip 70 are overlapped with the elastic part of the outer flap 42, and a force to pull out the outer flap 42 in the lateral direction X can be transmitted on the entire elastic part of the outer flap 42, and thus part of the outer flap 42 positioned in the crotch region 13 can also be pulled out in the lateral direction X. In the illustrated embodiment, while the elastic part of the outer flap 42 are formed of a single of the elastic member 61, the elastic part may be formed of multiple elastic members arranged spacedly in the lateral direction X so that the elastic part may have a stable configuration thereby to come in planar contact with the wearer's thigh.

With reference to FIG. 5, to achieve the above-described advantageous effects of the embodiments according to the present invention, a dimension L4 in the longitudinal direction Y at the overlapped part 78 of the inner end 71 of the elastic strips 70 and the side elastic part having the elastic member 61 of the outer flap 42 in planar view is about 3.0 mm to about 7.0 mm, preferably about 5.0 mm. As used here, the term "overlapped part" means including the instance where, while the inner end 71 of the elastic strip 70 is not completely overlapped with the elastic member 61 of the outer flap 42 in planar view, they are slightly spaced apart from each other so that they can function elastically in cooperation with each other.

The absorbent panel 30 may have a pair of the inner flaps 39. The inner flaps 39 are each positioned inward in the lateral direction X of the inner end 71 of the elastic strip 70 fixed to the body facing surface of the outer flap 42. When the diaper 10 is worn, the inner flap 71 may from a barrier cuff by spacing away from the bodyside liner 31 toward the wearer's thigh under construction of the elastic member 61, while the outer flap may come in planar contact with the wearer's thighs by being pulled out in the lateral direction X toward the thigh, and thus the outer flap 42 can effectively prevent body exudates from leaking sideways with at least part of the outer flap 42 extended in the longitudinal and lateral directions Y and X.

As described above, to ensure that the outer flaps 42 are pulled out in the lateral direction X when the diaper is worn, each tensile stress of the elastic strips 70 is preferable to be higher than each tensile stress of the front and rear waist elastic areas. If each tensile stress of the elastic strips 70 is lower than each tensile of the front and rear waist elastic areas, when the front and rear waist regions 11 and 12 are stretched in the waist circumference direction, the elastic strips 70 may be stretched its full length prior to the front waist elastic area or the rear waist elastic area being stretched. Thus, the front and rear waist elastic areas are not stretched in the desired dimension (e.g., a 65% to 80% extended state from a non-extended state when the diaper is not worn) by stopping stretching, and thus the front and rear waist regions may not be stretched so as to come in close contact with the wearer's waist. The tensile stress of the elastic strip 70 may be substantially equal to the tensile stress of the front waist elastic area or the rear waist elastic area. As used herein, "the tensile stress of the elastic strip 70 may be substantially equal to the tensile stress of the front waist elastic area or the rear waist elastic area" means including the instance where, in addition to both tensile stresses being equal to each other, there is a difference of about 10% in consideration of the deviation between a design tensile stress value and an actual tensile stress value which may occur in the product manufacturing process.

<Measuring Method for Tensile Stress>

Measuring for tensile stresses of the elastic strips 70 and the front waist elastic area (or the rear waist elastic area) was carried out by a cycle test using a tensile testing machine (e.g., Autograph Tensile Test Machine (AG-1KNI) of Kabushiki Kaisha SHIMADZU Manufacturing).

First, test strips 1 and 2 were each obtained and measured by the following procedure. Each test strip 1: a red mark was put on the front waist elastic area (or the rear waist elastic area) along the contour of the elastic strips 70, and the elastic strips 70 were removed from the diaper 10 by releasing the fixing of the temporal fixing sites 75 and the inner and outer fixed ends 71 and 72. Next, test strip 2: the red marked area of the front waist elastic area was cut out. Each test strip 1 and 2 were measured in a state stretched to the extent that gathers under contraction of elastic materials in each test strip do not occur, and the measured values were each set as a width dimension W1 at the maximum extension of the test strip. Next, one end of each test strip was fixed by the fixing jig (chuck) and the other was fixed by the moveable jig (chuck), after each test strip was stretched up to 90% stretch rate (90% of the width) at a rate of 300 mm/min in the stretching direction of each test strip (the lateral direction X), each test strip was backed up to a length of 70% stretch rate at a rate of 300 mm/min, and a value measured in this way was set as a tensile stress value (N) of each test strip.

The tensile stresses of the elastic strips 70 in the lateral direction X as determined by the above measurement were about 0.1 N to 1.5 N, and the tensile stress of the front waist elastic area (the rear waist elastic area) in the lateral direction X as determined by the above measuring was about 1.0 N to about 2.0 N.

The outer fixed ends 72 of the elastic strips 70 disposed in the front and rear waist regions 11 and 12 may extend to the respective side seams 16, and may be joined by heat-welding with the inner and outer layers 21 and 22 and the elastic strips 70 overlapped with each other. The welded joining of the outer fixed ends may have higher joining strength than the case where the outer fixed ends 72 are joined with adhesive, and thus the elastic strips 70 may not be removed during the diaper 10 is transported and worn.

However, although not illustrated, as long as the respective outer fixed ends 72 of the elastic strips 70 have the required joining strength, the respective outer fixed ends 72 may be positioned on the body facing surface of the chassis 20 inside in the lateral direction X of the respective side seams 16. In this instance, respective dimensions W2 in the lateral direction X of the elastic strips 70 are preferable to be more than 50% of respective separation dimensions in the lateral direction X of from the respective inner fixed ends 71 to the respective side seams 16. If the respective dimensions W2 of the elastic strips 70 are less than 50% of such respective separation dimensions, the respective elastic areas of the elastic strips 70 become relatively small in their dimensions in the lateral direction X, and thus the respective elastic areas may not exert stretching forces enough to pull out the respective outer flaps 42 in the lateral direction X.

Figure 8:
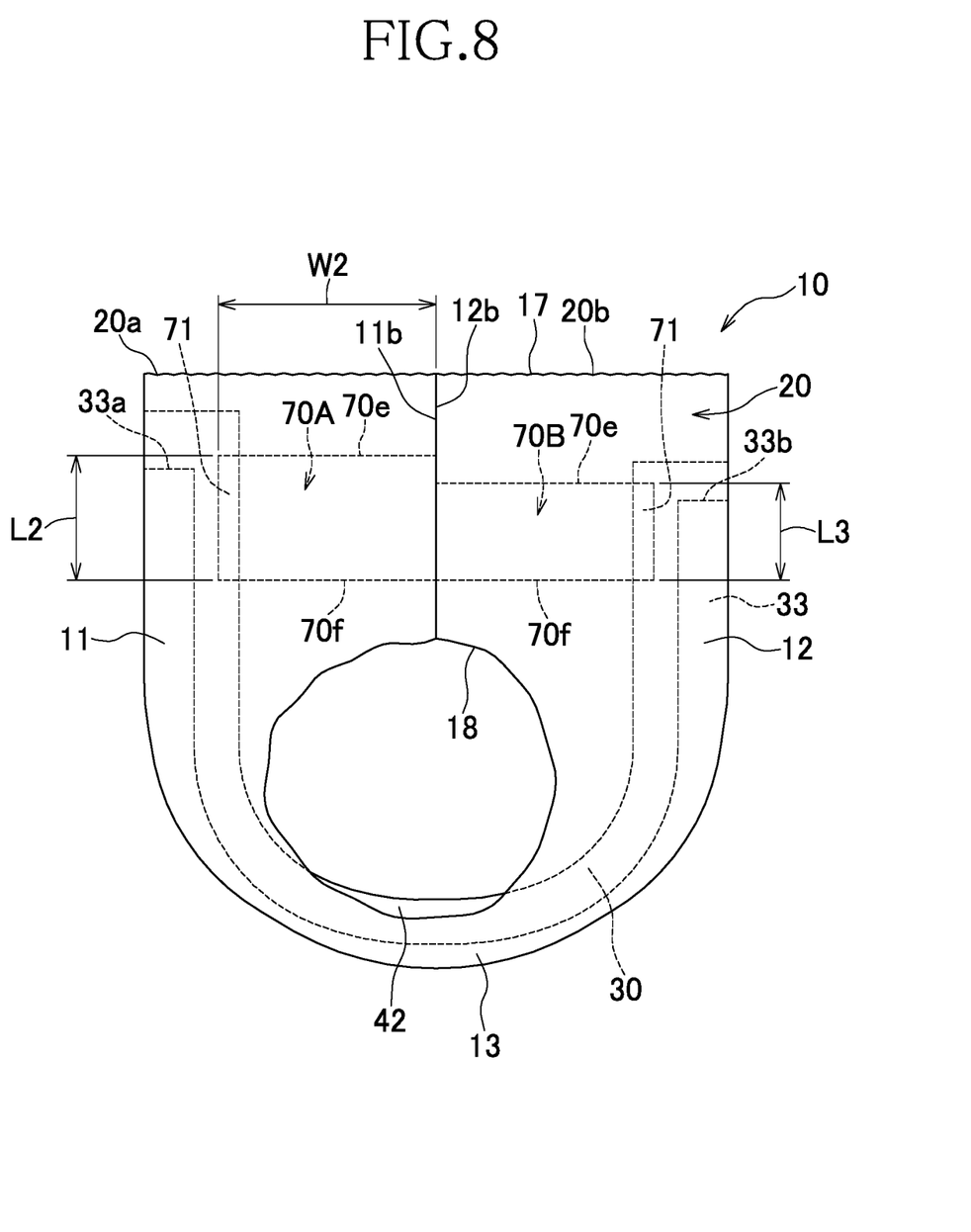
FIG. 8 illustrates a schematic view of one side of the disposable diaper.

With reference to FIGS. 2 and 8, the elastic strips 70A disposed in the front waist region 11 and the elastic strip 70B disposed in rear waist region 12 are each joined to each other at the side seams 16 so that the elastic strips 70A and 70B can contiguously extend to each other in the waist circumferential direction. Thus, when the diaper is put on the wearer, the respective elastic strips 70A and 70B can pull out the outer flaps 42 in the lateral direction X, and the elastic strips 70A and 70B are arranged facing each other in the front-rear direction; therefore, they can pull out the outer flaps 42 in a well-balanced state in the lateral direction X.

A dimension L2 of the elastic strip 70A disposed in the front waist region 11 is larger than a dimension L3 of the respective elastic strip 70A disposed in the rear waist region 12. Specifically, the dimension L2 is about 40 mm to about 60 mm, the dimension L3 is about 30 mm to 50 mm. In the diaper 10 according to the present preferred embodiment, the absorbent core 33 is entirely biased to the front side so that a distance dimension between the front end edge 33a of the absorbent core 33 and the front end edge 20a of the chassis 20 is smaller than a distance dimension between the rear end edge 33b of the absorbent core 33 and the rear end edge 20b of the chassis 20, and the front end edge 33a is positioned higher than the rear end edge 33b in the worn state of the diaper. In such position arrangement of the absorbent core 33, the elastic strip 70A having a width thereof comparatively widened can cover the front end edge 33a and reduce a level difference and a sharp change of sheet layer stiffness produced in the vicinity of the front end edge 33a. Further, as long as the respective elastic strips 70A and the respective elastic strips 70B are arranged facing each other in the front-rear direction in the worn state of the diaper, while the dimensions L2 and L3 may be equal to each other or the dimension L3 may be larger than the dimensions L2, the elastic strips 70A disposed in the front waist region 11 is preferable to be comparatively widen. This makes it possible to fit the front waist region 11 such as gently wrapping the wearer's abdominal region. As used herein, "the dimension L2 may be equal to the dimension L3" means including the instance where there is a difference of about 10% in consideration of the deviation between a design dimension and actual product dimension which may occur in the manufacturing process.

<Measurement of Degree of Stretching of Area Including Elastic Strip>

Figure 9A:
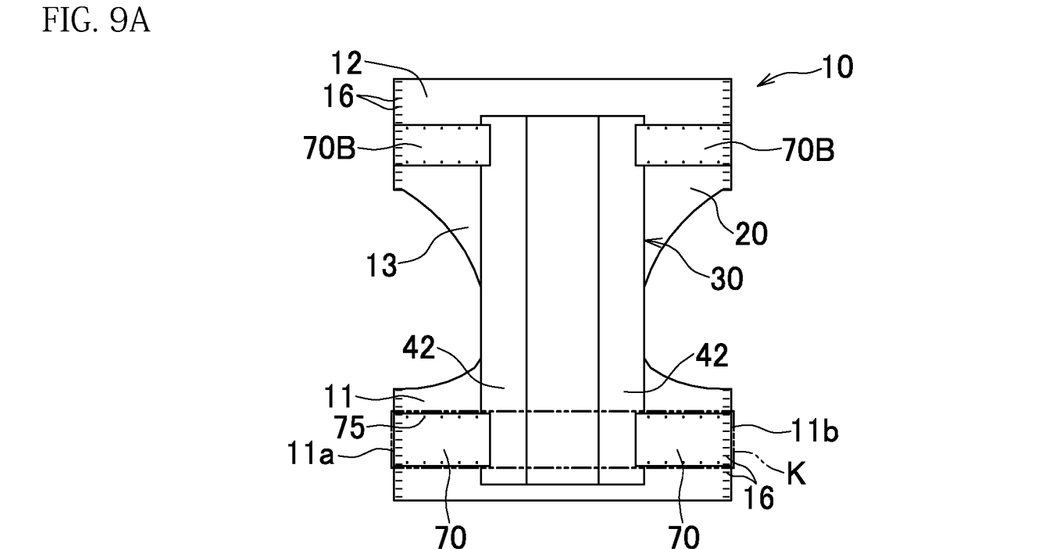
FIG. 9A illustrates an opened plan view of the diaper used for measuring an elastic degree of a first elastic part and a second elastic part.
Figure 9B:
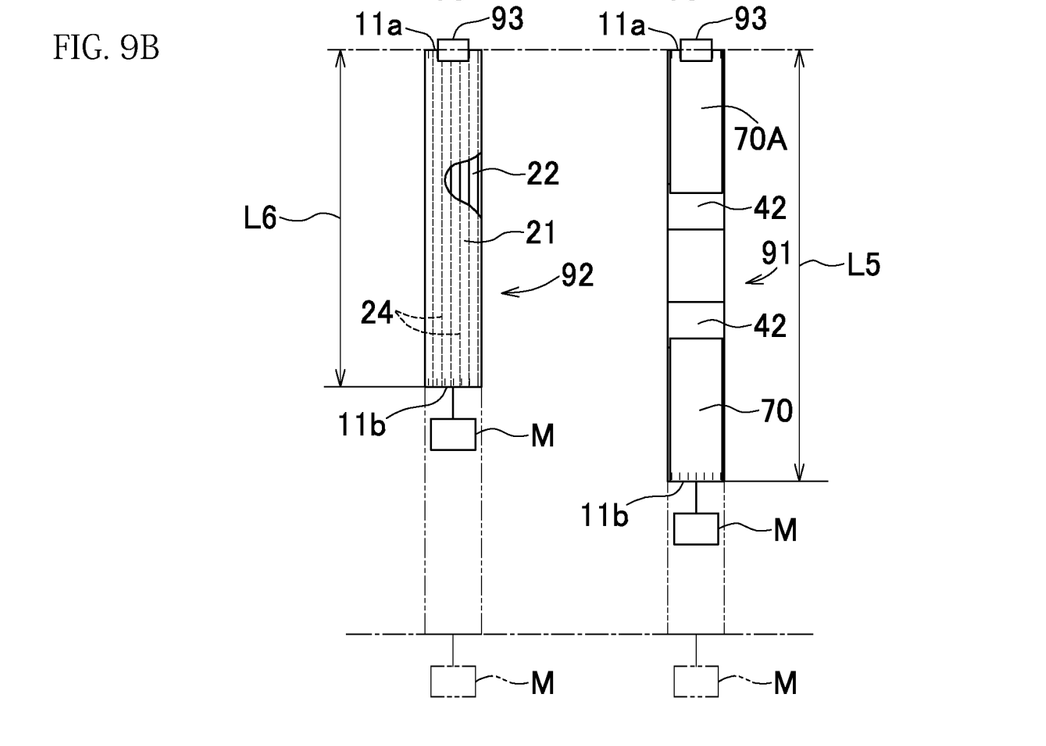
FIG. 9B illustrates a contracted state the first elastic part and the second elastic part cut off from the diaper.

FIG. 9A illustrates an opened plan view of the diaper 10 used for measuring a degree of stretching of a first elastic portion 91 and a second elastic portion 92 including a pair of elastic strips, and FIG. 9B illustrates a contracted state of a first elastic portion 91 and a second elastic portion 92 respectively cut out from the diaper 10.

With reference to FIG. 9A, the area K extending in the lateral direction X between both side edges 11a and 11b of the front waist region 11 of the diaper 10 was marked and cut out, the temporal fixing sites 75 of the elastic strips 70A were removed from the front waist region 11, the side seams 16 were opened, and then the joined part of the chassis 20 and the absorbent panel 30 was peeled off. Whereby the area K were separated into the first elastic portion 91 and the second elastic portion 92. Thus, the first elastic portion 91 was formed of a pair of elastic strips 70A and a part of the absorbent panel 30 positioned therebetween, and the second elastic portion 92 was formed of a part of the chassis 20 (including inner and outer layer sheets 21 and 22 and multiple front waist elastic members 24 secured therebetween) which faced the first elastic portion 91 in the thickness direction.

With reference to FIG. 9B, as shown by a solid line, in a state hanging the first elastic portion 91 and the second elastic portion 92 while fixing their respective one ends to fixing jigs 93, weights M (for example, weights M of lightweight (5 g for example) were attached to the other ends of the first and second elastic portions 91 and 92 for stabilizing the configurations of still maintaining the contacted states of them. In the contracted state of the first and second elastic portions 91 and 92, a dimension L5 in the lateral direction X of the first elastic portion 91 was larger than a dimension L6 in the lateral direction X of the second elastic portion 92, and in a state before the diaper 10 was worn, a portion excluding a part of the absorbent panel 30 fixed to the chassis 20 of the first elastic portion 91, that is, the pair of elastic strips 70A and 70B was in a relaxed state. On the other hand, as shown by a chain line, in a state attached to the respective other ends of the first and second elastic portions 91 and 92 with weights M having a load to the extent that gathers was not formed on the surface of the first and second elastic portions 91 and 92, the dimension L5 of the first elastic portion 91 and the dimension L6 of the second elastic portion 92 was approximately the same as each other.

If the pair of elastic strips 70 is stretched to their full lengths when the waist opening is opened to put the diaper 10 on a wearer, such full lengths may inhibit stretching of the front and rear waist regions 11 and 12 to stop stretching. However, in the state before the diaper 10 is put on the wearer, the portion excluding the part of the absorbent panel 30 fixed to the chassis 20 of the first elastic portion 91, that is, the pair of elastic strips 70A and 70B is a relaxed state, and he elastic strips 70 do not inhibit stretching of the front and rear waist regions 11 and 12. This allows the front and rear waist regions 11 and 12 to stretch to exert a moderate holding force to the body of a wearer.

Second Embodiment

Figure 10:
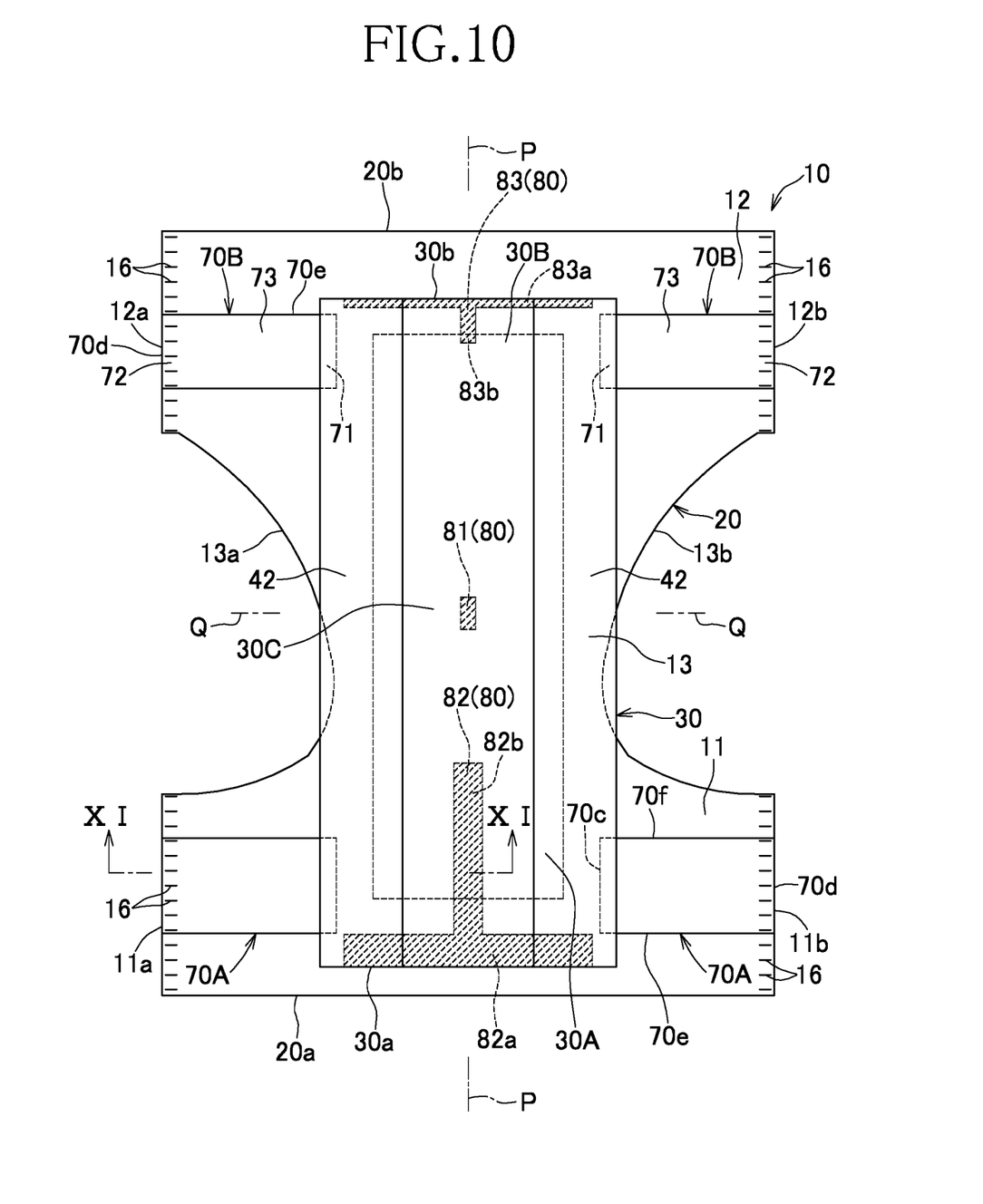
FIG. 10 illustrates an opened plan view similar to FIG. 2 of the diaper according to the second embodiment.
Figure 11:
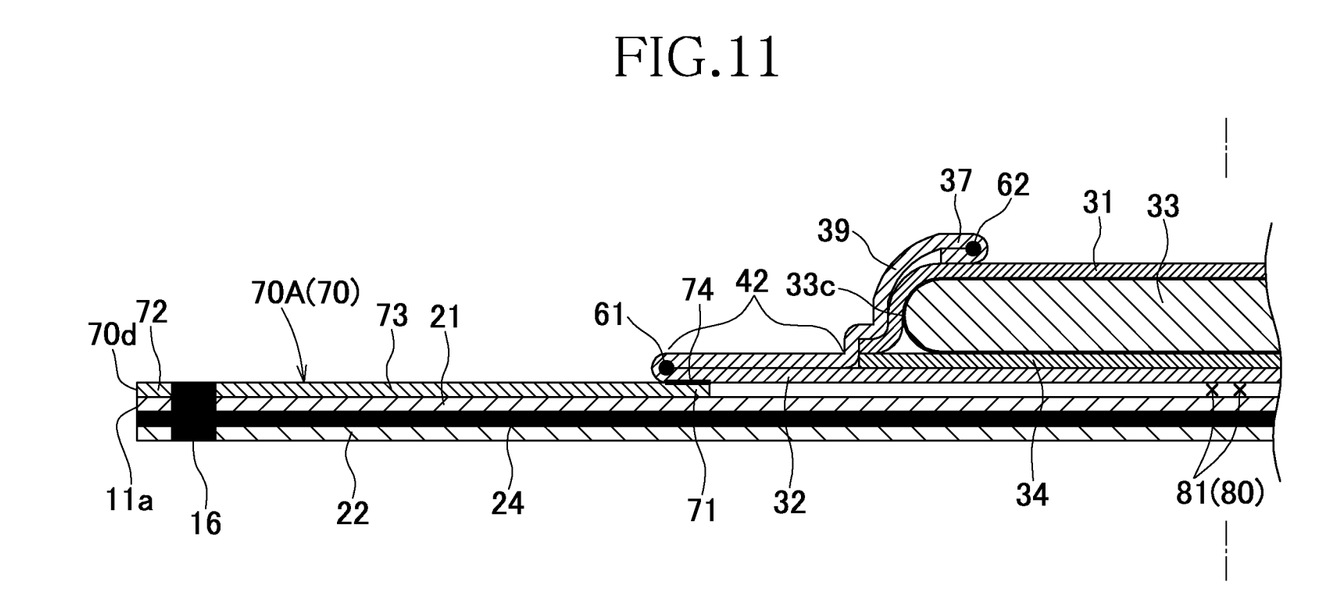
FIG. 11 illustrates an exploded view along X-X line in FIG. 10.

FIG. 10 illustrates an opened plan view similar to FIG. 2 of the diaper 10 according to the first embodiment, and FIG. 11 illustrates an exploded view along X-X line in FIG. 10. The basic configuration of the diaper 10 according to the first embodiment is the same as that of the diaper 10 according to the second embodiment, and only different points are described below.

With reference to FIGS. 10 and 11, in this embodiment, unlike the first embodiment, the absorbent panel 30 is joined to the chassis 20 with hot-melt adhesive applied to a part of the surface of the chassis 20 facing the absorbent panel 30 without applying hot-melt adhesive to the entire surface of the chassis 30 facing the absorbent panel 30. The joining area 80 has a middle fixing area 81 in a generally longitudinal rectangular form for fixing the middle 30C of the absorbent panel 30 and both end fixing areas 82 and 83 for respectively fixing the front and rear ends 30A and 30B. Both end fixing areas 82 and 83 respectively have generally T-shapes and lateral fixing portions 82a and 83a extending in the lateral direction along the front and rear end edges 30a and 30b, and longitudinal fixing portions 82b and 83b extending toward the lateral center line Q-Q along the longitudinal center line P-P from the lateral fixing portions 82a and 83a. The longitudinal front end portion 82b of the front end fixing area 82 has a width and a length larger than those of the longitudinal fixing area 83, and extend adjacent to the crotch region 13 from the front waist region 11. Thus, the front end 30A of the absorbent panel 30 is more stably fixed to the chassis 20 than the rear end 30B of the absorbent panel 30. As long as the absorbent panel 30 has the required joining strength, the middle fixing area 81 of the joining area 80 may not be provided and only both end fixing areas 82 and 83 may be provided.

In the present preferred embodiment including such a joining manner of the absorbent panel 30, the outer flaps 42 may be positioned in an unfixing area on the chassis 20, in other words, the outer flaps 42 are not fixed to the fixing area, while the inner fixing ends 71 of the elastic strips 70 are fixed to the non-body facing surface (the surface facing the chassis 20) of the outer flap 42. The absorbent panel 30 is in a state such as being hanged by the chassis 20 due to being partially fixed to the chassis 20 at the joining area 80, and may positionally be displaced during wearing of the diaper, the respective outer flaps 42 may be positioned inside of the respective leg openings 18 without extending outward across the respective leg openings 18 or twisted, so that the respective outer flaps 42 may not come in planar contact with the wearer's highs. However, each pair of elastic strips 70A and 70B may be disposed on the front and rear waist regions 11 and 12, and such trouble such as the positional displacement can be prevented. In other words, the absorbent panel 30 may be pulled in the lateral direction X opposite to each other by elastically stretching of the elastic strips 70A and 70B during wearing of the diaper, and the center of the absorbent panel 30 may be positioned on the longitudinal line P or therealong, and the absorbent panel 30 may be inhibited to shift on either of the positions left and right. Further, the inner fixing ends 71 are fixed to the outer flap 42, and the outer flaps 42 may be pulled outward in the lateral direction X so as to come in planar contact with the wearer's thighs.

Further, unlike the first embodiment, the inner fixing end 71 is fixed to the non-body facing surface of the outer flap 42, and the parts of the outer flap 42 and elastic strip 70 which are stiffer by the joining part 71 may not come in direct contact with the wearer's skin, and may be inhibited to create a discomfort feeling against the wearer. In the present preferred embodiment, while the absorbent panel 30 is described about the instance in which the absorbent panel 30 is partially fixed to the chassis 20 by joining area 80, even if the entire surface of the absorbent panel 30 facing the chassis 20 is fixed with hot-melt adhesive similarly to the first embodiment, the area in the vicinity of the outer side edge 42a of the outer flap 42 is often designed as an unfixing area in the manufacturing process of the diaper 10 to prevent extrusion of hot-melt adhesive outward. Such instance may be included in one of the embodiments according to the present invention.

Unless otherwise noted, the construction elements of the diaper 10 are not limited to those described in the description and the claims but other various types of materials widely used in the relevant technical filed may be used without limitation. As used herein, the terms "first" and "second" of the description and claims are used merely to distinguish the similar elements, similar parts or other matters.

The invention claimed is:

1. A disposable wearing article having a longitudinal direction and a lateral direction, the article comprising a chassis including a body facing surface, a non-body facing surface, a first waist region which is one of front and rear waist regions, a second waist region which is another of the front and rear waist regions and a crotch region extending between the first and second waist regions, an absorbent panel disposed on a side of the body facing surface of the chassis, and both side seams respectively coupling both side edges of the first waist region and both side edges of the second waist region, respectively, wherein:

the absorbent panel includes an absorbent core extending to the front and rear waist regions centering on the crotch region, a pair of outer flaps extending longitudinally along both side edges of the absorbent core, at least the first waist region of the first and second waist regions includes a waist elastic area which is elastically contractible in the lateral direction, and a pair of elastic strips which is elastically contractible in the lateral direction, each of the pair of elastic strips has an inner fixing end fixed to the outer flap of the absorbent panel and an outer end fixing end fixed to the body facing surface of the chassis.

2. The disposable wearing article according to claim 1 wherein the outer flap of the absorbent panel is fixed to the body facing surface of the chassis, and the inner fixing end of the elastic strip is fixed to the body facing surface of the outer flap.

3. The disposable wearing article according to claim 1 wherein at least a part of the outer flap is unfixed to the body facing surface of the chassis, and the inner fixing end of the elastic strip is fixed to the non-body facing surface of the outer flap.

4. The disposable wearing article according to claim 1 wherein a tensile stress in the lateral direction of the elastic strip is higher than a tensile stress in the lateral direction of the waist elastic area.

5. The disposable wearing article according to claim 1 wherein the outer flap of the absorbent panel includes a side elastic area which is elastically contractible in the longitudinal direction, and the inner fixing end of the elastic strip is overlapped with the side elastic area in planar view.

6. The disposable wearing article according to claim 1 wherein the outer fixing end of the elastic strip is positioned inside in the lateral direction of the seam, and a dimension in the lateral direction of the elastic strip is more than 50% of a space dimension of from the inner fixing end to the seam.

7. The disposable wearing article according to claim 1 wherein the outer fixing end of the elastic strip extends to the seam.

8. The disposable wearing article according to claim 1 wherein the absorbent panel includes a pair of barrier cuffs, and the barrier cuffs are each positioned more inside in the lateral direction than the inner fixing end of the elastic strip.

9. The disposable wearing article according to claim 1 wherein the elastic strip is more outside in the longitudinal direction than an end in the longitudinal direction of the absorbent core.

10. The disposable wearing article according to claim 1 wherein the pair of elastic strips is disposed on the second waist region, and the pair of elastic strips positioned on the first waist region and the pair of elastic strips positioned on the second waist region are respectively joined to each other at the side seams.

11. The disposable wearing article according to claim 1 wherein the pair of elastic strips is disposed on the second waist region, and a dimension in the longitudinal direction of each of the elastic strips positioned on the first waist region is equal to or larger than a dimension in the longitudinal direction of each of the elastic strips positioned on the second waist region.

12. The disposable wearing article according to claim 1 wherein the elastic strips are temporally fixed to the body facing surface of the chassis.

* * * * *